United States Patent
Hansenne

[11] Patent Number: 6,030,629
[45] Date of Patent: Feb. 29, 2000

[54] PHOTOPROTECTIVE COSMETIC/ DERMATOLOGICAL COMPOSITIONS COMPRISING SYNERGISTIC ADMIXTURE OF SUNSCREEN COMPOUNDS

[75] Inventor: Isabelle Hansenne, Paris, France

[73] Assignee: Societe L'Oreal S.A., Paris, France

[21] Appl. No.: 09/028,359

[22] Filed: Feb. 24, 1998

[30] Foreign Application Priority Data

Feb. 24, 1997 [FR] France .................. 97 02162

[51] Int. Cl.$^7$ .................. A61K 7/06; A61K 7/42
[52] U.S. Cl. .................. 424/401; 424/59; 424/60; 424/70.9
[58] Field of Search .................. 424/401, 450, 424/59, 60, 63, 69, 70.1, 70.9, 78.03; 514/938; 528/12; 568/331

[56] References Cited

U.S. PATENT DOCUMENTS 5,607,664  3/1997  Ascione et al. .................. 424/59
5,618,520  4/1997  Hansenne et al. .................. 424/59
5,753,209  5/1998  Ascione et al. .................. 424/59

FOREIGN PATENT DOCUMENTS

94/06404  3/1994  WIPO .

Primary Examiner—Jeffrey E. Russel
Attorney, Agent, or Firm—Burns, Doane, Swecker & Mathis, L.L.P.

[57] ABSTRACT

Topically applicable sunscreen/cosmetic compositions well suited for enhanced SPF photoprotection of human skin and/or hair against the damaging effects of UV-A and UV-B irradiation, particularly solar radiation, comprise synergistically effective amounts of (i) particular benzotriazole-substituted silicon compounds and (ii) particular sulfonic/benzimidazole compounds, formulated into appropriate vehicles, diluents or carriers therefor, advantageously formulated as oil-in-water emulsions.

23 Claims, No Drawings

PHOTOPROTECTIVE COSMETIC/DERMATOLOGICAL COMPOSITIONS COMPRISING SYNERGISTIC ADMIXTURE OF SUNSCREEN COMPOUNDS

CROSS-REFERENCE TO PRIORITY APPLICATION

This application claims priority under 35 U.S.C. §119 of FR-02162, filed Feb. 24, 1997, hereby expressly incorporated by reference.

BACKGROUND OF THE INVENTION

1. Technical Field of the Invention

The present invention relates to novel topically applicable cosmetic and/or dermatological compositions well suited for the photoprotection of the skin and/or hair against the deleterious effects of ultraviolet radiation (such compositions hereinafter more simply referred to as "sunscreen" or "antisun" compositions).

This invention more especially relates to sunscreen compositions comprising, in a cosmetically acceptable support (vehicle, diluent or carrier), a combination of a first specific screening agent, namely, a specific sulfonic derivative of benzimidazole, and at least one second specific screening agent judiciously selected from among the benzotriazole silicones.

2. Description of the Prior Art

It is known to this art that light radiation of wavelengths of from 280 nm to 400 nm promotes tanning of the human epidermis, and that light irradiation of wavelengths more particularly ranging from 280 to 320 nm, i.e., UV-B irradiation, causes skin burns and erythema which may be harmful to the development of a natural tan. For these reasons, as well as for aesthetic reasons, there is a constant demand for controlling this natural tanning in order, thus, to control the coloration of the skin; this UV-B radiation must thus be screened from the skin.

It is also known to this art that UV-A radiation, of wavelengths of from 320 to 400 nm, which tans the skin, also adversely affects it, especially in the case of sensitive skin or of skin which is continually exposed to solar radiation. TV-A rays cause, in particular, a loss of elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, for aesthetic and cosmetic reasons such as conservation of the natural elasticity of the skin, for example, an ever-increasing number of individuals seek to control the effects of UV-A radiation on their skin. It is thus desirable to also screen UW-A radiation from the skin and/or hair.

A very wide variety of cosmetic compositions intended for the photoprotection (UV-A and/or UV-B) of the skin are known to this art.

These photoprotective compositions are typically oil-in-water emulsions (namely, a cosmetically acceptable vehicle, diluent or carrier comprising a continuous aqueous dispersing phase and a discontinuous oily dispersed phase) which contain, in various concentrations, one or more conventional lipophilic and/or hydrophilic organic screening agents capable of selectively absorbing harmful UV radiation. These screening agents (and the amounts thereof) are selected as a function of the desired sun protection factor (SPF) which is expressed mathematically by the ratio of the irradiation time required to reach the erythema-forming threshold with the UV screening agent, to the time required to reach the erythema-forming threshold without UV screening agent.

SUMMARY OF THE INVENTION

It has now surprisingly and unexpectedly been determined that a unique combination of two particular sunscreen active agents, formulated in certain well-defined proportions, provide novel photoprotective/sunscreen compositions having sun protection factors that are synergistically markedly improved and, in all instances, considerably superior to those which can be obtained either with one or the other of the screening agents employed individually, or, alternatively, using combinations simultaneously containing both screening agents but in ratios not according to the invention.

Briefly, the present invention features novel cosmetic and/or dermatological compositions, in particular antisun/sunscreen compositions which comprise, in a cosmetically acceptable vehicle, diluent or carrier, (i) at least one silicon sunscreen compound containing a benzotriazole function, comprising at least one structural unit of formula (1) below:

$$O_{(3-a)/2}Si(R)_a-A \quad (1)$$

in which R is an optionally halogenated $C_1$–$C_{10}$ alkyl radical, a phenyl radical, or a trimethylsilyloxy radical; a is an integer ranging from 0 to 3, inclusive; and the symbol A is a monovalent radical directly bonded to a silicon atom, and having the formula (2) below:

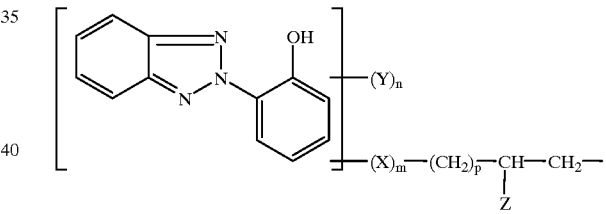

(2)

in which the radicals Y, which may be identical or different, are each a $C_1$–$C_8$ alkyl radical, a halogen atom, or a $C_1$–$C_4$ alkoxy radical, with the proviso that, in the latter instance, two adjacent radicals Y on the same aromatic ring member can together form an alkylidenedioxy moiety wherein the alkylidene group has 1 or 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive, and (ii) at least one sulfonic sunscreening derivative of benzimidazole C having the formula (3) below:

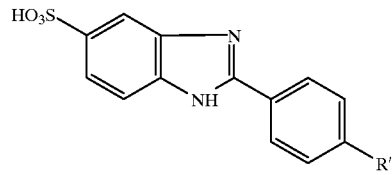

(3)

in which R' is a hydrogen atom, a linear or branched $C_1$–$C_8$ alkyl or alkoxy radical, or a radical of formula (4) below:

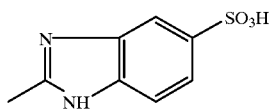

(4)

the said first and second screening agents being present in the said compositions in a molar ratio (A/C) providing a synergistic improvement in the SPF.

The present invention also features cosmetic and/or dermatological compositions well suited for the photoprotection of the skin and/or the hair against ultraviolet radiation, in particular solar radiation.

Too, this invention features a cosmetic treatment for photoprotecting the skin and/or the hair against the deleterious effects of ultraviolet radiation, in particular solar radiation, and which comprises topically applying an effective photoprotecting amount of a composition as described above to the skin and/or the hair.

DETAILED DESCRIPTION OF BEST MODE AND SPECIFIC/PREFERRED EMBODIMENTS OF THE INVENTION

More particularly according to the present invention, the silicon compounds (i) are characteristically silanes or siloxanes containing a benzotriazole function comprising at least one structural unit of formula (1) below:

$$O_{(3-a)/2}Si(R)_a\text{—}A \qquad (1)$$

in which R is an optionally halogenated $C_1$–$C_{10}$ alkyl radical, or a phenyl radical, or a trimethylsilyloxy radical; a is an integer ranging from 0 to 3, inclusive, and the symbol A is a monovalent radical directly bonded to a silicon atom and having the formula (2) below:

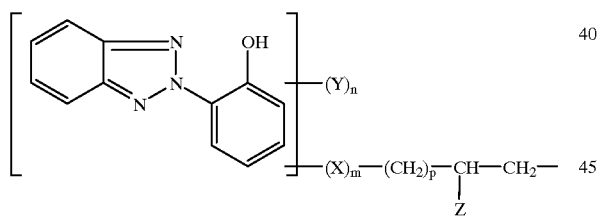

(2)

in which the radicals Y, which may be identical or different, are each a $C_1$–$C_8$ alkyl radical, a halogen atom, or a $C_1$–$C_4$ alkoxy radical, with the proviso that, in the latter instance, two adjacent radicals Y on the same aromatic ring member can together form an alkylidenedioxy moiety in which the alkylidene group has 1 or 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

These compounds are described, in particular, in EP-A-711,778 and in WO-94/06404, both assigned to the assignee hereof.

Preferably, the silicon compounds (i) according to the present invention belong to the general family of benzotriazole silicones which is described, in particular, in WO-94/06404. One family of benzotriazole silicones which is particularly suitable according to the present invention is that which includes the compounds having the formulae (5) or (6) below:

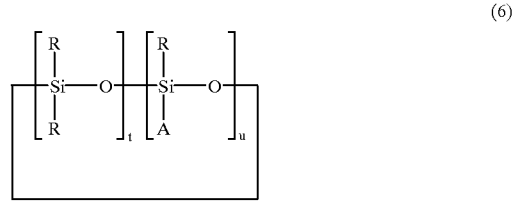

(5)

or

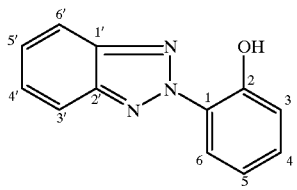

(6)

in which the radicals R, which may be identical or different, are each a $C_1$–$C_{10}$ alkyl, phenyl, 3,3,3-trifluoropropyl or trimethylsilyloxy radical, at least 80% by number of the radicals R being methyl radicals; the radicals B, which may be identical or different, are each a radical R or a radical A; r is an integer ranging from 0 to 50, inclusive; s is an integer ranging from 0 to 20, inclusive, with the proviso that if s=0, then at least one of the two radicals B is a radical A; u is an integer ranging from 1 to 6, inclusive; and t is an integer ranging from 0 to 10, inclusive, with the proviso that t+u is equal to or greater than 3; and the symbol A is as defined in formula (2) above.

As will be seen from formula (2) above, bonding of the radical chain —$(X)_m$—$(CH_2)_p$—$CH(Z)$—$CH_2$— to the benzotriazole nucleus which thus ensures bonding of said benzotriazole structural unit to a silicon atom of the silicone moiety may take place, according to the present invention, in all of the available positions presented by the two aromatic rings of the benzotriazole:

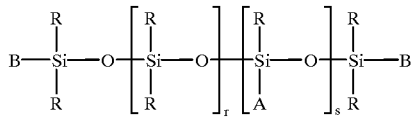

Preferably, this attachment is at position 3, 4, 5 (aromatic ring bearing the hydroxyl function) or 4' (benzene ring adjacent to the triazole ring), and even more preferably at position 3, 4 or 5. In a preferred embodiment of the invention, the attachment or bonding is at position 3.

Similarly, bonding of the substituent structural unit or units Y may be at all other available positions or sites in the benzotriazole. However, preferably, this attachment is at position 3, 4, 4', 5 and/or 6. In a preferred embodiment of the invention, bonding of the structural unit Y is at position 5.

In formulae (5) and (6) above, the alkyl radicals may be linear or branched and, advantageously, are selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R according to the invention are methyl, ethyl, propyl, n-butyl, n-octyl and 2-ethylhexyl radicals. Even more preferably, the radicals R are all methyl radicals.

Among the compounds of formula (5) or (6) above, preferred are those corresponding to formula (5), namely, diorganosiloxanes comprising a short linear chain.

Among the compounds of formula (5) above, preferred are those for which the radicals B are both radicals R.

Among the linear diorganosiloxanes according to the present invention, random derivatives or well-defined block derivatives having at least one, and even more preferably all, of the following characteristics are the preferred:

B is a radical R,

R is alkyl and even more preferably is methyl, r ranges from 0 to 15, inclusive, s ranges from 1 to 10, inclusive, n is other than zero and preferably is equal to 1, Y is methyl, tert-butyl or $C_1$–$C_4$ alkoxy, Z is hydrogen or methyl, m=0 or [m=1 and X=O], and p is equal to 1.

One class of benzotriazole silicones which is particularly suitable for the invention is that having the structural formula (7) below:

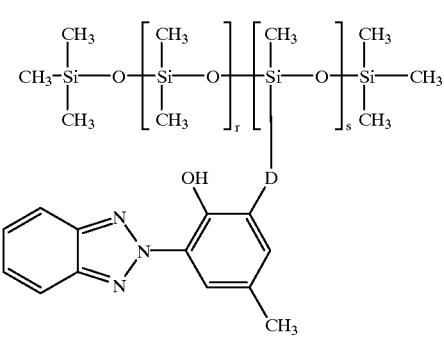
(7)

in which 0<r<10; 1≤s<10; and D is the divalent radical:

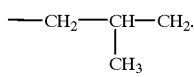

In a particularly preferred embodiment of the invention, the benzotriazole silicone is the compound (hereinafter referred to as compound A) having the following structural formula:

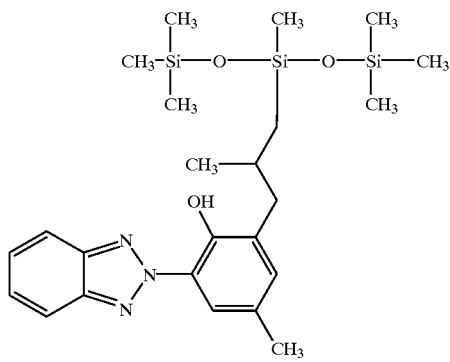

Processes which are suitable for the preparation of the compounds of formulae (1), (5), (6) and (7) above are described, in particular, in U.S. Pat. Nos. 3,220,972, 3,697,473, 4,340,709, 4,316,033 and 4,328,346 and in EP-A-0,392,883 and EP-A-0,742,003.

The silicon compound containing a benzotriazole function is advantageously present in the compositions of the invention in amounts ranging from 0.1% to 20% by weight, preferably from 0.2% to 15% by weight, relative to the total weight of the composition.

The sulfonic benzimidazole derivatives (compound C) according to the present invention are water-soluble compounds known for their excellent photoprotective capacity in the UV-B radiation range and corresponding to formula (3) below:

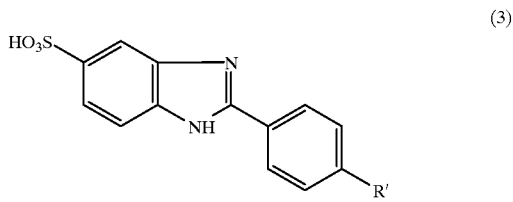
(3)

in which R' is a hydrogen atom, a linear or branched $C_1$–$C_8$ alkyl or alkoxy radical, or a radical of formula (4):

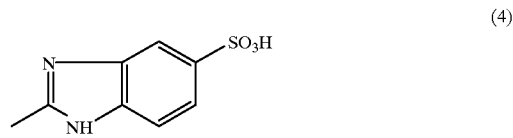
(4)

A sulfonic benzimidazole derivative which is particularly suitable for the compositions according to the invention is 2-phenylbenzimidazole-5-sulfonic acid, marketed under the trademark "Eusolex 232" by Merck, which has following structural formula:

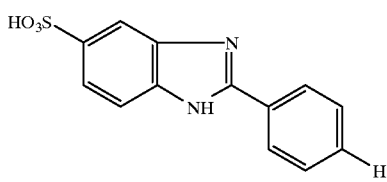

The sulfonic benzimidazole compound is advantageously present in the compositions of the invention in amounts ranging from 0.1% to 10%, preferably from 0.1% to 5%, by weight, relative to the total weight of the composition.

From a practical standpoint, the above two screening agents, namely, the silicon compound containing a benzotriazole structural unit and the sulfonic benzimidazole derivative, are, obviously, preferably both present in the final composition in respective proportions selected such that the synergistic effect, as regards the sun protection factor imparted by the resulting combination, is optimal.

These proportions can vary depending on the number of benzotriazole structural unit(s) borne by the silicon derivative containing a benzotriazole function. Thus, preferably, in the present invention, the [(benzotriazole unit of the first screening agent)/sulfonic benzimidazole derivative] molar ratio, i.e., the (A/C) molar ratio, advantageously ranges from 1/20 to 10/3, preferably from 1/10 to 5/2, even more preferably from 2/5 to 3/5.

Thus, in the specific case in which the first screening agent according to the present invention is silicone compound A of formula (7) above and the second screening agent according to the invention is the sulfonic benzimidazole derivative marketed under the trademark "Eusolex 232", the [(first screening agent)/(second screening agent)] weight ratio advantageously ranges from 1/10 to 6/1, preferably from 1/4 to 4/1. Even more preferably, this weight ratio is 1/1.

Lastly, also according to a preferred embodiment of the present invention, the subject compositions are emulsions of oil-in-water type.

The sunscreen cosmetic compositions according to the invention can also contain one or more additional hydrophilic or lipophilic sunscreens that are active in the UVA and/or UVB range (absorbers) other than, of course, the two screening agents indicated above. These additional screening agents can be selected, in particular, from among cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the screening polymers and screening silicones described in WO-93/04665. Other examples of organic screening agents are set forth in EP-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or nanopigments (average size of the primary particles: generally ranging from 5 nm to 100 nm, preferably from 10 nm to 50 nm) of coated or uncoated metal oxides, such as for example, nanopigments of titanium dioxide (amorphous or crystallized in rutile and/or anatase form), of iron oxide, of zinc oxide, of zirconium oxide or of cerium oxide which are all UV-photoprotective agents that are well known to this art. Standard coating agents include, moreover, alumina and/or aluminum stearate. Such coated or uncoated metal oxide nanopigments are described, in particular, in EP-A-0,518,772 and EP-A-0,518,773.

The compositions of the invention may also comprise standard cosmetic adjuvants and additives selected, in particular, from among fatty substances, organic solvents, ionic or nonionic thickeners, softeners, antioxidants, opacifying agents, stabilizers, emollients, silicones, α-hydroxy acids, anti-foaming agents, moisturizers, vitamins, fragrances, preservatives, surfactants, fillers, sequestering agents, polymers, propellants, basifying or acidifying agents, insect repellent, dyes or colorants, or any other ingredient usually used in cosmetics, in particular for the formulation of sunscreen compositions in the form of emulsions.

The fatty substances may be an oil or a wax or mixtures thereof, and may also comprise fatty acids, fatty alcohols and fatty acid esters. The oils may be selected from among animal, plant, mineral or synthetic oils and, in particular, from liquid petrolatum, liquid paraffin, volatile or non-volatile silicone oils, isoparaffins, poly-u-olefins, fluoro oils and perfluoro oils. Similarly, the waxes may be selected from among animal, fossil, plant, mineral or synthetic waxes that are known per se.

Exemplary organic solvents include the lower alcohols and polyols.

Exemplary thickeners include, in particular, crosslinked polyacrylic acids and modified or unmodified guar gums and cellulose gums such as hydroxypropyl guar gum, methylhydroxyethylcellulose, hydroxypropylmethylcellulose or hydroxyethylcellulose.

It will be apparent that one skilled in this art will take care to select the optional complementary compound or compounds indicated above and/or the amounts thereof such that the advantageous properties, especially the synergistic effect, intrinsically associated with the binary combination in accordance with the invention are not, or are substantially not, adversely affected by the addition or additions envisaged.

The compositions of the invention are formulated according to techniques which are well known to this art, in particular those utilized for the preparation of emulsions of oil-in-water or water-in-oil type.

Such compositions may be, in particular, in simple or complex emulsion form (O/W, W/O, O/W/O or W/O/W), such as a cream, a milk, a gel or a cream-gel, a powder or a solid stick and may optionally be packaged as an aerosol, or may be in the form of a foam or a spray.

When the subject compositions are formulated as emulsions, the aqueous phase thereof may comprise a non-ionic vesicle dispersion prepared according to known techniques (Bangham, Standish and Watkins, *J. Mol. Biol.*, 13, 238 (1965), FR-2,315,991 and FR-2,416,008).

The cosmetic compositions of the invention are useful for protecting human skin and/or hair against the deleterious effects of ultraviolet irradiation, as sunscreen compositions or as makeup products.

When the cosmetic compositions according to the invention are used for protecting human skin against UV irradiation or as sunscreens, they are advantageously formulated as suspensions or dispersions in solvents or in fatty substances, as nonionic vesicle dispersions or, alternatively, as emulsions, preferably of oil-in-water type, such as a cream or a milk, or are formulated as ointments, gels cream-gels, solid sticks, sticks, aerosol foams or sprays.

When the cosmetic compositions according to the invention are used to protect the hair, they are advantageously formulated as shampoos, lotions, gels, emulsions, nonionic vesicle dispersions or lacquers for the hair and may constitute, for example, a rinseout composition to be applied before or after shampooing, before or after dyeing or bleaching, before, during or after permanent-waving or straightening of the hair, a styling or treating lotion or gel, a blow-drying or hair-setting lotion or gel, or a composition for permanent-waving, straightening, dyeing or bleaching the hair.

When the subject compositions comprise a makeup product for the eyelashes, the eyebrows or the skin, such as a skin treatment cream, a foundation, a lipstick, an eyeshadow, a blusher, a mascara or an eyeliner, they may be formulated in anhydrous or aqueous, solid or pasty form, for example oil-in-water or water-in-oil emulsions, nonionic vesicle dispersions or suspensions.

For example, in the sunscreen formulations in accordance with the invention which comprise a vehicle, diluent or carrier of oil-in-water emulsion type, the aqueous phase (in particular comprising the hydrophilic screening agents) typically constitutes from 50% to 95% by weight, preferably from 70% to 90% by weight, relative to the total weight of the formulation, the oily phase (in particular comprising the lipophilic screening agents) from 5% to 50% by weight, preferably from 10% to 30% by weight, relative to the total weight of the formulation, and the (co)emulsifying agent(s) from 0.5% to 20% by weight, preferably from 2% to 10% by weight, relative to the total weight of the formulation.

As hereinabove indicated, the present invention features a cosmetic treatment for the skin or the hair which is intended to protect same against the damaging effects of UV radiation, this regime or regimen comprising topically applying an effective photoprotecting amount of a cosmetic composition consistent herewith to the skin or the hair.

In order to further illustrate the present invention and the advantages thereof, the following specific examples are given, it being understood that same are intended only as illustrative and in nowise limitative.

EXAMPLE 1

Various sunscreen formulations in the form of oil-in-water type emulsions were prepared containing (the amounts are expressed in % by weight relative to the total weight of the composition):

Phase A1:

| Compound A (benzotriazole silicone) | y% |
| --- | --- |
| Mixture of glyceryl stearate and PEG-100 stearate marketed under the trademark "Arlacel 165" by ICI | 1.5% |
| Stearic acid marketed under the trademark "Stearine TP" by Stéarinerie Dubois | 2.75% |
| Cetyl alcohol marketed under the trademark "Lorol C16" by Henkel | 0.5% |
| $C_{12}$–$C_{15}$ alkyl benzoate marketed under the trademark "Finsolv TN" by Finetex | 15% |
| Preservatives | qs |

Phase A2:

| Triethanolamine | 0.45% |
| --- | --- |

Phase B:

| 2-Phenylbenzimidazole-5-sulfonic acid marketed under the trademark "Eusolex 232" by Merck | x% |
| --- | --- |
| Potassium cetyl phosphate marketed under the trademark "Amphisol K" by Givaudan-Roure | 1% |

Phase C:

| Crosslinked polyacrylic acid marketed under the trademark "Carbopol 980" by Goodrich | 0.3% |
| --- | --- |

Phase D:

| Triethanolamine | qs |
| --- | --- |

Phase E:

| Hydrating agent | 5% |
| --- | --- |
| Preservatives | qs |
| Water | qs 100% |

Each of the above emulsions was formulated in the following manner: phases A1 and A2 were preheated and homogenized with stirring at 80° C. Phase E was introduced into the manufacturing tank and heated to 80° C. with stirring. Phases B and C were then dispersed in phase E for 30 minutes. The mixture (A1+A2) was added, with vigorous stirring, to the aqueous phase (E+B+C). The mixture was stirred for 15 minutes. This mixture was then cooled to 50° C. and phase D was added. The entire mixture was cooled to 25° C.

For each of these formulations, the sun protection factor (SPF) associated therewith was then determined. This was accompanied via the in vitro technique described by B. L. Diffey et al., in *J. Soc. Cosmet. Chem.*, 40, 127–133 (1989); this technique entailed determining the monochromatic protection factors every 5 nm over a wavelength range from 290 to 400 nm and in calculating, from these factors, the sun protection factor according to a given mathematical equation.

The compositions of the various formulations studied and the results in terms of average sun protection factor (average of three tests) obtained are reported in the Tables below.

TABLE I

Comparative formulae A to F

| Screening agent | Formula A | Formula B | Formula C | Formula D | Formula E | Formula F |
| --- | --- | --- | --- | --- | --- | --- |
| x (%) | 1 | 0 | 2.5 | 0 | 4 | 0 |
| y (%) | 0 | 4 | 0 | 2.5 | 0 | 1 |
| SPF | 3.7 | 6.8 | 5.2 | 4.5 | 8.5 | 2.4 |

TABLE II

Formulae G, H and J according to the invention

| Screening agent | Formula G | Formula H | Formula J |
| --- | --- | --- | --- |
| X (%) | 1 | 2.5 | 4 |
| Y (%) | 4 | 2.5 | 1 |
| y/x weight ratio | 4 | 1 | 0.25 |
| (Benzotriazole/benzimidazole) molar ratio | 2.183 | 0.546 | 0.136 |
| Average SPF | 11.2 | 17.8 | 13.2 |

Thus, for an overall concentration of screening agents of 5% by weight, the following results were obtained:

SPF(formula A)+SPF(formula B)=10.5 SPF(formula G)=11.2

SPF(formula C)+SPF(formula D)=9.7 SPF(formula H)=17.8

SPF(formula E)+SPF(formula F)=10.9 2SPF(formula J)=13.2

These results clearly demonstrate the surprising synergistic effects obtained with compositions G, H and J in accordance with the invention.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen composition suited for the photoprotection of human skin and/or hair, comprising photoprotecting synergistically effective amounts of (i) at least one silicon compound containing a benzotriazole functional group and which comprises at least one structural unit of formula (1):

$$O_{(3-a)/2}Si(R)_a\text{—}A \tag{1}$$

in which R is an optionally halogenated $C_1$–$C_{10}$ alkyl radical, or a phenyl or trimethylsilyloxy radical; a is an integer ranging from 0 to 3, inclusive; and the symbol A is a monovalent radical directly bonded to a silicon atom, having the structural formula (2):

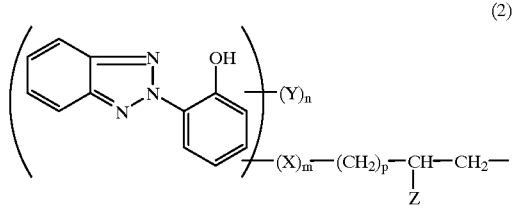
(2)

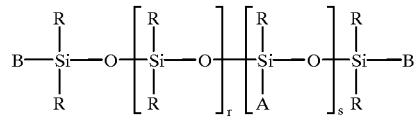
(5)

or

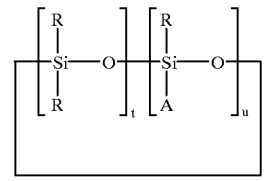
(6)

in which the radicals Y, which may be identical or different, are each a $C_1$–$C_8$ alkyl radical, a halogen atom, or a $C_1$–$C_4$ alkoxy radical, with the proviso that, in the latter instance, two adjacent radicals Y on the same aromatic ring member can together form an alkylidenedioxy moiety in which the alkylidene group has 1 or 2 carbon atoms; X is O or NH; Z is hydrogen or a $C_1$–$C_4$ alkyl radical; n is an integer ranging from 0 to 3, inclusive; m is 0 or 1; p is an integer ranging from 1 to 10, inclusive; and (ii) at least one sulfonic sunscreening derivative of benzimidazole C having the formula (3):

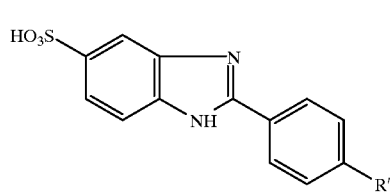
(3)

in which R' is a hydrogen atom, a linear or branched $C_1$–$C_8$ alkyl or alkoxy radical, or a radical of formula (4) below:

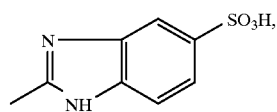
(4)

wherein the molar ratio of said at least one compound (i) to said at least one compound (ii) ranges from 1/20 to 10/3.

2. The sunscreen composition as defined by claim 1, wherein the molar ratio of said at least one compound (i) to said at least one compound (ii) ranges from 1/10 to 5/2.

3. The sunscreen composition as defined by claim 1, wherein the molar ratio of said at least one compound (i) to said at least one compound (ii) ranges from 2/5 to 3/5.

4. The sunscreen composition as defined by claim 1, said at least one silicon/benzotriazole compound (i) having the following structural formulae (5) or (6):

in which the radicals R, which may be identical or different, are each a $C_1$–$C_{10}$ alkyl, phenyl, 3,3,3-trifluoropropyl or trimethylsilyloxy radical, at least 80% by number of said radicals R being methyl radicals; the radicals B, which may be identical or different, are each a radical R or a radical A; r is an integer ranging from 0 to 50, inclusive; s is an integer ranging from 0 to 20, inclusive, with the proviso that if s=0, then at least one of the two radicals B is a radical A; u is an integer ranging from 1 to 6, inclusive; and t is an integer ranging from 0 to 10, inclusive, with the proviso that t+u is equal to or greater than 3; and the symbol A is as defined in formula (2).

5. The sunscreen composition as defined by claim 4, said at least one silicon/benzotriazole compound (i) having the structural formula (7):

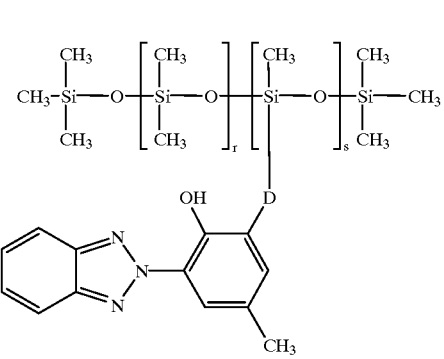
(7)

in which $0 \leq r \leq 10$; $1 \leq s \leq 10$; and D is the divalent radical:

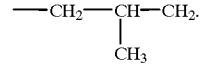

6. The sunscreen composition as defined by claim 1, said at least one sulfonic/benzimidazole compound (ii) comprising 2-phenylbenzimidazole-5-sulfonic acid.

7. The sunscreen composition as defined by claim 1, said at least one silicon/benzotriazole compound (i) having the structural formula:

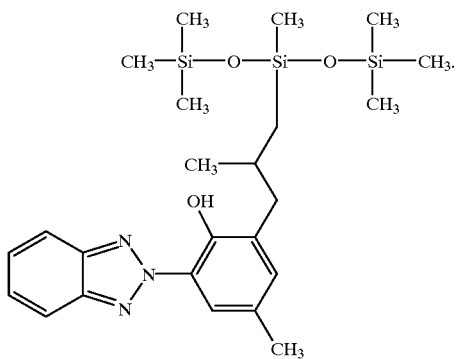

8. The sunscreen composition as defined by claim 7, wherein the ratio by weight of said at least one silicon/benzotriazole compound (i) to said at least one sulfonic/benzimidazole compound (ii) ranges from 1/10 to 6/1.

9. The sunscreen composition as defined by claim 7, wherein the ratio by weight of said at least one silicon/benzotriazole compound (i) to said at least one sulfonic/benzimidazole compound (ii) ranges from 1/4 to 4/1.

10. The sunscreen composition as defined by claim 7, wherein the ratio by weight of said at least one silicon/benzotriazole compound (i) to said at least one sulfonic/benzimidazole compound (ii) is about 1.

11. The sunscreen composition as defined by claim 1, comprising from 0.1% to 20% by weight of said at least one silicon/benzotriazole compound (i).

12. The sunscreen composition as defined by claim 11, comprising from 0.2% to 15% by weight of said at least one silicon/benzotriazole compound (i).

13. The sunscreen composition as defined by claim 11, comprising from 0.1% to 10% by weight of said at least one sulfonic/benzimidazole compound (ii).

14. The sunscreen composition as defined by claim 12, comprising from 0.1% to 5% by weight of said at least one sulfonic/benzimidazole compound (ii).

15. The sunscreen composition as defined by claim 1, further comprising at least one additional hydrophilic or lipophilic organic UV-A and/or UV-B sunscreen.

16. The sunscreen composition as defined by claim 1, further comprising at least one active agent for the artificial tanning and/or browning of human skin.

17. The sunscreen composition as defined by claim 1, further comprising at least one additive or adjuvant which comprises a fat, organic solvent, ionic or nonionic thickening agent, softener, antioxidant, anti-free radical antioxidant, opacifying agent, stabilizing agent, emollient, silicone, u-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

18. The sunscreen composition as defined by claim 1, comprising a nonionic vesicle dispersion, emulsion, cream, milk, gel, cream gel, ointment, suspension, dispersion, powder, solid, stick, foam or spray.

19. The sunscreen composition as defined by claim 1, comprising a makeup.

20. The sunscreen composition as defined by claim 1, comprising an anhydrous or aqueous solid or paste, emulsion, suspension, or dispersion.

21. The sunscreen composition as defined by claim 1, comprising a shampoo, lotion, gel, emulsion, nonionic vesicle dispersion, hair lacquer, or rinse.

22. A method for protecting human skin and/or hair against the deleterious effects of ultraviolet irradiation, comprising topically applying thereto an effective amount of the sunscreen composition as defined by claim 1.

23. A method for protecting human skin and/or hair against the deleterious effects of solar radiation, comprising topically applying thereto an effective amount of the sunscreen composition as defined by claim 1.

* * * * *